United States Patent
Brock-Fisher et al.

(10) Patent No.: US 6,692,442 B2
(45) Date of Patent: Feb. 17, 2004

(54) DEVICE FOR PRODUCING AN ON-LINE IMAGE OF A BODY PART INTO WHICH A CONTRASTING AGENT HAS BEEN INTRODUCED

(75) Inventors: George Brock-Fisher, Andover, MA (US); Patrick G. Rafter, Windham, NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/022,173

(22) Filed: Dec. 13, 2001

(65) Prior Publication Data

US 2003/0114750 A1 Jun. 19, 2003

(51) Int. Cl.$^7$ ................................................. A61B 8/00
(52) U.S. Cl. ....................................................... 600/458
(58) Field of Search ................................. 600/443, 444, 600/448, 437, 458, 460, 455, 447, 449, 461, 459

(56) References Cited

U.S. PATENT DOCUMENTS 5,146,924 A    9/1992  Sepponen ................. 128/653.2
6,231,834 B1   5/2001  Unger et al. ................ 424/9.51
6,258,033 B1 * 7/2001  Grenon ......................... 600/458
6,352,511 B1 * 3/2002  Hossack et al. ............. 600/443
6,377,832 B1 * 4/2002  Bergman et al. ............. 600/408
6,397,098 B1 * 5/2002  Uber et al. .................. 600/431
6,419,632 B1 * 7/2002  Shiki et al. .................. 600/443

FOREIGN PATENT DOCUMENTS

WO    WO 01/01865    11/2001    ............ A61B/8/00

* cited by examiner

*Primary Examiner*—Francis J. Jaworski
*Assistant Examiner*—Maulin Patel
(74) *Attorney, Agent, or Firm*—John Vodopia

(57) ABSTRACT

The present invention relates to a] A device for producing an image of a body part into which a contrasting agent has been introduced, the device including an image detecting device modifying the contrasting agent to provide a modified image, and a processor acquiring and processing the modified image so as to create an image which represents a rate of flow of blood or other fluid in the body part. The device may be an ultrasound imaging device or may be a magnetic resonance imaging device.

37 Claims, 3 Drawing Sheets

DEVICE FOR PRODUCING AN ON-LINE IMAGE OF A BODY PART INTO WHICH A CONTRASTING AGENT HAS BEEN INTRODUCED

BACKGROUND OF THE INVENTION

1. Field of the Invention

The present invention relates to a device for producing an on-line image of a body part into which a contrasting agent has been introduced, and more particularly, to an ultrasound device which detects the contrasting agent in the body part and produces an on-line display of the results for analysis of fluid flow into the body part.

2. Description of the Related Art

With regard to the basic concept of ultrasound, an ultrasound device makes a frame out of a plurality of lines and ultrasound waves are transmitted in different directions. Typically, this is done at a rate of 30 to 60 frames per second. Specifically in relation to the heart, a doctor or technician looks at how the heart beats in real time by making a real time picture of the heart where one can see it contracting. What ultrasound has tried to do in the past is to try to see functionally whether the walls of the heart are moving and determine from that whether there is blood getting to the heart tissue. On the ultrasound image, blood is dark as it is made out of red blood cells and the heart tissue is very bright. The heart tissue scatters back the ultrasound with a significant amount of energy, whereas the blood does not really scatter the ultrasound much. Upon viewing an ultrasound image of the heart, the heart tissue would appear somewhat speckly and bright and the blood would appear fairly dark. Techniques have been known that look at the blood and how it moves, for example using color flow in Doppler. But a two-dimensional image typically looks very bright for the heart tissue and one would not see anything in the chambers of the heart.

Further, the doctor or technician may be concerned about a stenosis or blockage in the heart and want to determine blood flow in the heart. The above techniques result in indirect measures of blood flow in the heart tissue, e.g., the myocardium. However, more direct techniques of determined blood flow are desired.

Another technique, which is more direct, involves injecting a contrasting agent, which has little microbubbles, into the vein of a subject. The microbubbles are small enough to make it through the capillaries of the subject. The microbubbles are basically some type of shell, like albumen, plastic or sugar, and contain a gas like air or nitrogen or perfluorocarbon. All these microbubbles scatter back the ultrasound by making the blood more echogenic. With these microbubbles, the doctor or technician wants to watch where the blood travels in the tissue.

Since this is a more direct way of looking at whether there is a blood flow problem, such a technique is more sensitive and a better test than looking at the motion of the heart. The main concept behind using contrast agents with ultrasound is to enable a doctor or technician to see blood flow in the heart.

If there is a blockage in the heart, there is going to be less of these microbubbles flowing into various portions of the heart, such as the myocardium. Different parts of the heart that are fed by different coronary arteries would be affected by the blockage. If one part of the ultrasound image is dark and another part is bright, the doctor or technician would know that there probably is a problem with the coronary artery that feeds the dark part of the heart.

Upon studying the use of contrasting agents with ultrasound, it was discovered that the ultrasound destroyed the microbubbles. By destroying the microbubbles and watching how fast they come back, the doctor or technician could determine not only how many microbubbles are in any part of the heart, she could determine how fast they were moving, which is the blood flow. By destroying the microbubbles and then timing how fast they come back, it is possible to determine which areas of the heart have slow flow and which areas have rapid flow, through a determination of how quickly the number of microbubbles change in the various parts of the heart.

A high powered frame of an ultrasound is emitted from the ultrasound device to destroy the microbubbles and lower powered frames of the ultrasound are emitted to watch the microbubbles come back. Different timing arrangements may be usable to determine the blood flow using a contrasting agent having the microbubbles.

The blood flow can be modeled as an exponential where blood flow equals $A(1-e^{bt})$. It is well known to discuss perfusion after the microbubbles have been destroyed based on the value A.

FIG. 1 is a diagram showing a conventional system which uses a contrasting agent to analyze blood flow in different parts of the body, particularly the heart. A contrasting agent is injected into a vein of a patient so as to flow in the blood stream. An ultrasound machine 10 transmits ultrasound signals to a desired portion of the body, or more particularly, a desired portion of the heart, and receives the reflected ultrasound signals. The transmitted ultrasound signals are varied in intensity, with a high intensity burst destroying the microbubbles of the contrasting agent and lower intensity bursts not destroying the microbubbles. The reflected ultrasound signals are detected to determine the number of microbubbles present in the portion of the heart at a particular point in time, and then displayed, with the screen being brighter as the number of microbubbles increases.

The data relating to the number of microbubbles for various portions of the heart over time may be stored in a recording medium, such as a floppy disk or a compact disk or another medium. The recording medium would then be placed in a computer 20 and an analysis would be performed in the computer 20 to determine blood flow in a portion or in portions of the heart.

Alternatively, the ultrasound machine 10 could be connected to the Internet 30. Instead of storing the data in the recording medium as set forth immediately above, the data relating to the number of microbubbles for various portions of the heart over time would be transmitted over the Internet 30 and stored in an external location such as a website. The data would then be processed at the website, and the analysis would be performed to determine the blood flow in a portion or in portions of the heart.

The conventional technique is an extremely time consuming process and does not provide the doctor or technician with all the feedback she wants. A significant amount of processing is done off line to produce an image with a color overlay of white, grey, black, etc. In addition, this process takes a significant amount of time, so that if the ultrasound is not being performed properly during the time of receiving the ultrasound information, it would not be known until later that the procedure was improper and the subject would either have to have the ultrasound device applied to her again after waiting for the off line results or the subject would have to come back at a later date to reconduct the ultrasound test.

SUMMARY OF THE INVENTION

The present invention relates to a device for producing an image of a body part into which a contrasting agent has been introduced, the device comprising an image detecting device modifying the contrasting agent to provide a modified image, and a processor acquiring and processing the modified image so as to create an image which represents a rate of flow of blood or other fluid in the body part. The device may be an ultrasound imaging device or may be a magnetic resonance imaging device.

The processor processes the modified image on line or in real time, to more quickly enable a viewing of the blood or other fluid flow in the body part of concern, and quickly determine whether the test is being properly conducted.

BRIEF DESCRIPTION OF THE DRAWINGS

These and other objects and advantages of the invention will become apparent and more readily appreciated from the following description of the preferred embodiments, taken in conjunction with the accompanying drawings of which.

DESCRIPTION OF THE PREFERRED EMBODIMENTS

Reference will now made in detail to the present preferred embodiments of the present invention, examples of which are illustrated in the accompanying drawings. The embodiments are described below in order to explain the present invention by referring to the figures.

The present invention relates to ways to provide an on line or real time analysis and display of blood flow in portions of the heart using an ultrasound machine and a contrasting agent, instead of using an ultrasound machine to determine numbers of microbubbles in portions of the heart over time, and then moving off line and analyzing the results to determine the blood flow. The real time feedback is very advantageous over having to transmit the data to a computer or the Internet and wait the 20 minutes that is required to conduct the analysis off line.

Figure 1:
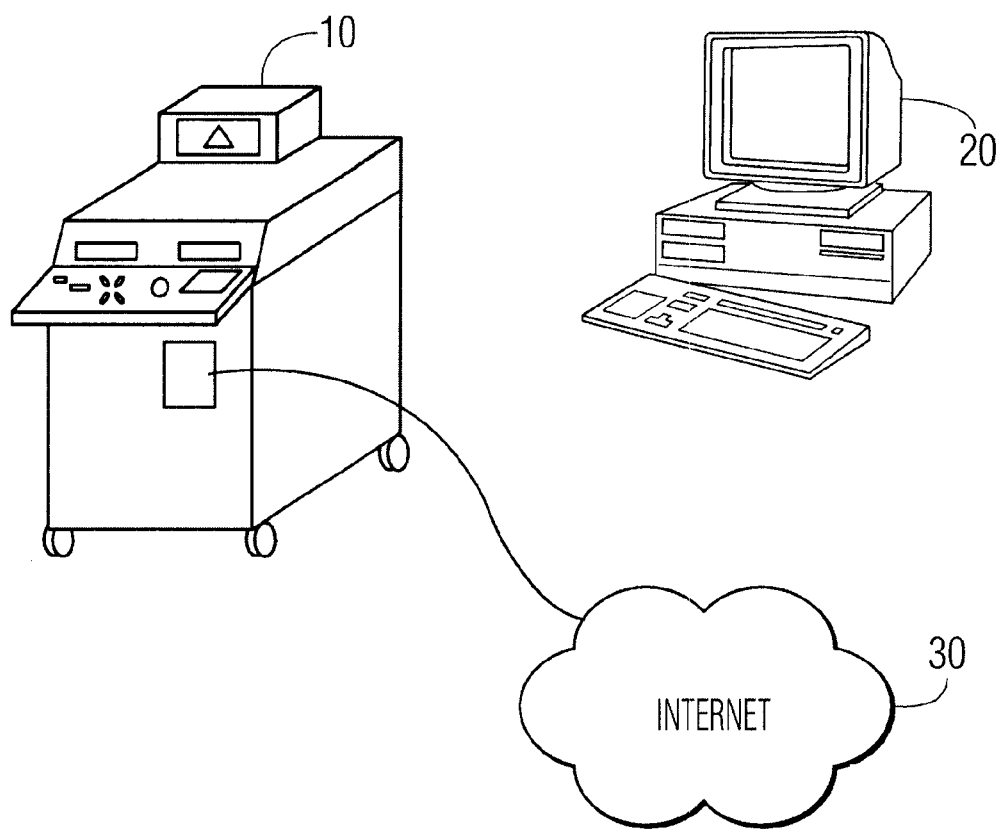
FIG. 1 is a diagram showing a conventional system which uses contrasting agents to analyze blood flow in different parts of the body, particularly the heart.
Figure 2:
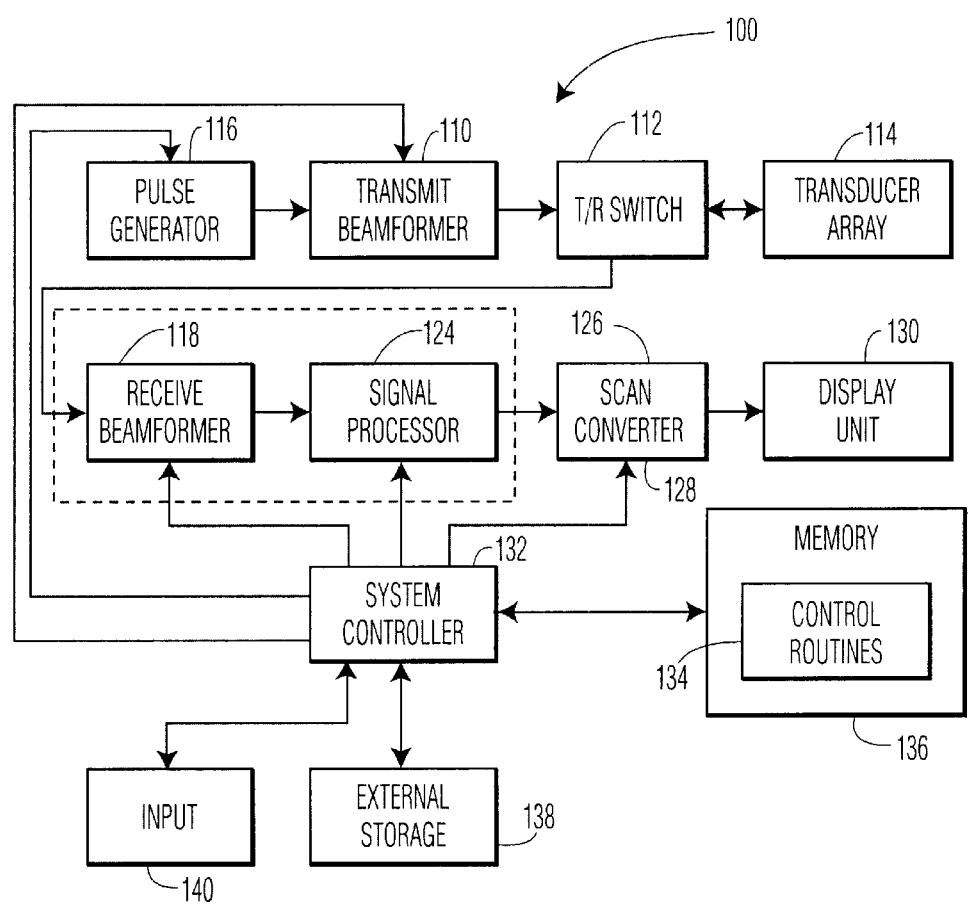
FIG. 2 is a block diagram of an ultrasound imaging system for use with embodiments of the present invention.

FIG. 2 is a block diagram of an ultrasound imaging system 100 for use with embodiments of the present invention. It will be appreciated by those of ordinary skill in the relevant arts that the ultrasound imaging system 100, as illustrated in FIG. 2, and the operation thereof as described hereinafter is intended to be generally representative of such systems and that any given system may differ significantly from that shown in FIG. 1, particularly in the details of construction and operation of such system. As such, the ultrasound imaging system 100 is to be regarded as illustrative and exemplary and not limiting as regards the invention described herein or the claims attached hereto.

A transmit beamformer 110 is coupled through a transmit/receive (T/R) switch 112 to a transducer array 114, which includes an array of transducer elements. The T/R switch 112 typically has one switch element for each transducer element. The transmit beamformer 110 receives pulse sequences from a pulse generator 116. The transducer array 114, energized by the transmit beamformer 110, transmits ultrasound energy into a region of interest (ROI) in a patient's body and receives reflected ultrasound energy, or echoes, from various structures and organs within the patient's body. As is known in the art, by appropriately delaying the waveforms applied to each transducer element by the transmit beamformer 110, a focused ultrasound beam is transmitted.

The transducer array 114 is also coupled, through the T/R switch 112, to a receive beamformer 118. Ultrasound energy from a given point within the patient's body is received by the transducer elements at different times. The transducer elements convert the received ultrasound energy to transducer signals which may be amplified, individually delayed and then summed by the receive beamformer 118 to provide a beamformer signal that represents the received ultrasound level along a desired receive line. The receive beamformer 118 may be a digital beamformer including an analog-to-digital converter for converting the transducer signals to digital values. As known in the art, the delays applied to the transducer signals may be varied during reception of ultrasound energy to effect dynamic focusing. The process is repeated for multiple scan lines to provide signals for generating an image of the region of interest in the patient's body. The receive beamformer 118 may, for example, be a digital beamformer of the type used in the AGILENT SONOS 5500 ultrasound system manufactured and sold by PHILIPS ELECTRONICS N.A. CORP.

The scan pattern may be a sector scan, wherein scan lines typically originate at the center of the transducer array 114 and are directed at different angles. Linear, curvilinear and other scan patterns may also be utilized. Furthermore, the scan pattern may be two-dimensional or three-dimensional. In an alternative system configuration, different transducer elements are used for transmitting and receiving. In that configuration, the T/R switch 112 is not required, and the transmit beamformer 110 and the receive beamformer 118 are connected directly to the respective transmit and receive transducer elements.

The beamformer signals are applied to a signal processor 124 which processes the beamformer signal for improved image quality and may include processes such as harmonic processing. The receive beamformer 118 and the signal processor 124 constitute an ultrasound receiver 126. The output of the signal processor 124 is supplied to a scan converter 128 which converts sector scan or other scan pattern signals to conventional raster scan display signals. The output of the scan converter 128 is supplied to a display unit 130, which displays an image of the region of interest in the patient's body. In the case of a three-dimensional scan pattern, the scan converter 118 may be replaced by an image data buffer that stores the three-dimensional data set and a processor that converts the three-dimensional data set to a desired two-dimensional image.

A system controller 132 provides overall control of the system. The system controller 132 performs timing and control functions and typically includes a microprocessor operating under the control of control routines 134, stored in a memory 138. As will be discussed in detail below, the control routines 134 include a variety of routines to process images and determine amounts of blood and blood flow in various parts of the body. The system controller 132 also utilizes a memory 136 to store intermediate values, including system variables describing the operation of the ultrasound imaging system 100. External storage 138 may be utilized for more permanent and/or transportable storage of data. Examples of devices suitable for use as the suitable external storage 138 include a floppy disk drive, a CD-ROM drive, a videotape unit, etc.

An input unit 140 provides an operator interface using a combination of input devices, such as keys, sliders, switches, touch screens and track balls.

Advantages of the ultrasound imaging system 100 include the ability to perform on line analysis and real time analysis. In this application, "on line" means that the entire analysis is performed on the ultrasound imaging system 100. There is no need for a separate PC such as the computer 20 in FIG. 1, and there is no need to transfer the data from the ultrasound imaging system 100 somehow to another processing station such as through the Internet 30 also shown in FIG. 1 or some other type of network. Thus, the data does not have to be removed from the ultrasound system, in other words, the data does not have to be transferred to a remote location. "On line" could also mean that a user interface device which is part of the ultrasound system such as a keyboard, mouse or pointer which is already present on the ultrasound system is used for determining blood flow when using a contrasting agent. In this case, the same graphical user interface is used.

"Real time" means that it appears from the point of view of a person that an image on a screen of the ultrasound imaging system 100 represents the actual condition of a patient at a particular instant in time, even though it may take a very small but finite amount of time for the system to process the information and display the same. This real time analysis is in contrast to the conventional system described in FIG. 1, where one must first store an image and then perform an analysis to determine the blood flow in a distinctly noticeable amount of time and then redisplays the image in a processed format.

A more detailed description of the ultrasound imaging system 100 will now be provided. The transducer array, through the control routines 134, may transmit an impulse, a high powered frame to destroy the microbubbles of the contrasting agent in the myocardium, another portion of the heart or elsewhere in the body, and then transmit a number of low power frames to allow the microbubbles to flow back to the region under consideration. This process occurs over 10, 20 cardiac cycles so it could take a long time for the blood to come back. In a healthy heart, this time is usually five to six cardiac cycles, wherein each cycle may be about one second. It could take 10 seconds, 20 seconds, etc.

In another technique, every time the transducer array 114 transmits a high power frame, one can see the microbubbles as they are destroyed, so the transducer array 114 waits one cardiac cycle to transmit another high powered frame and then waits another cardiac cycle and transmits another high powered frame and that will reveal the amount of microbubbles that return in one cardiac cycle. This process can done for two, three or more cardiac cycles, to determine how fast the micro microbubbles come back.

The flow of blood, and hence the microbubbles, into the myocardium or another part of the heart is generally modeled as an exponential according to the formula $A(1-e^{bt})$. Often, discussion in this field relates to perfusion after the microbubbles have been destroyed based on the variable (slope) b and these terms are used often.

In the conventional system shown in FIG. 1, data would be acquired regarding the number of microbubbles and a doctor or technician would move off line and try to determine the blood flow on the computer 20, by perhaps drawing a region of interest and move the region around because the heart is moving, to try to determine the above exponential curve. Such a process is very time consuming and does provide the desired feedback. The result is that the doctor or technician determines the number of microbubbles present over many regions, perhaps all of the regions of the heart and then tries to assemble one picture which describes the blood flow throughout the heart.

However, in the ultrasound imaging system 100 shown in FIG. 2, all of the processing to determine blood flow is performed according to the control routines 134 using the signal processor 124.

One of the ways one of the control routines 134 determines the blood flow is by subtracting consecutive frames of images of the portion(s) of the heart such as the myocardium which show the number of microbubbles present therein, to provide slopes between points. This can be done on a pixel by pixel basis over the entire field of view. Thus, the system might have some level of brightness in one position and in the next frame might have a greater level of brightness. By subtracting these frames, the control routine 134 determines the slope b which is related to the blood flow in the myocardium or other portion of the heart.

As ultrasound is very noisy, it is desirable to smooth out the images so as to minimize noise when the subtraction is performed. Subtractions tend to be noisy and ultrasound is noisy. When subtracting images, speckle occurs. With ultrasound images, upon being viewed, they have small areas of bright spots and dark spots so if the heart moves just a small amount, many of these small areas will appear if two consecutive frames are subtracted, and the result is a lot of noise. These speckles are due to coherent and incoherent interference. Even when there are no microbubbles, and the signal processor 125 is just subtracting two consecutive frames, there is a lot of noise. So it is very advantageous to smooth this out with a spatial filter to reduce the speckle.

Another process relates to alignment. One of the problems of subtracting images is that the speckle moves as the heart moves. The heart is pumping and the patient is breathing. If the frames are close together, part of the problem is the heart changes shape, so it might not be possible to completely align and subtract the images. However, to improve the images, one of the control routines 134 takes a plurality of images and aligns them before further processing. Over certain parts of the cardiac cycle, the heart is fairly steady, contracts and stops and expands and stops. It may be possible to only take images over some parts of the cardiac cycle, to perform the image alignment unless the image rate is so fast that consecutive frames are not that much different from each other. But there is the problem that to do this procedure from frame to frame, at different parts of the cardiac cycle, the heart may have changed shapes.

By using the same part of the cardiac cycle and aligning the image at one of those times with the next one, at least the heart would be the same or close to the same shape. The heart could still move because the patient is breathing, the heart rate might have changed, and the transducer array 114 moves, so some additional alignment is still needed. The timing may be based on the QRS complex end-diastole so that the end-diastole frames are processed together, or based on the end-systole so that the end-systole frames are processed together. In addition, more than one part of the cardiac cycle may be used. For example, all the end-diastole frames and all the end-systole frames may be processed together. The alignment is extremely beneficial prior to further processing. The alignment may be achieved according to a process including but not limited to translation, rotation, warping, expansion dilation, and other usual image processing techniques which may be model based.

Generally, the images may be aligned, smoothed, processed, and then displayed. The processing would be a subtraction.

It is also possible to do a colorized overlay or any other coding. The ultrasound imaging system 100 may include a control so that the colorized overlay could be turned on/off. Further, it is possible to have a display with the colorized overlay on at one side of the display and off at the other side of the display. It could be intensity instead of color, like a gray-scale intensity. There are also synchronization issues and selecting which frames would be present in the analysis and/or in the output issues. In other words, one technique might process all of the frames and the alignment algorithm would include some warping or something to maximize their ability to line up even though the heart is changing shape and so forth. Another technique would be selecting only certain phases, identical phases of the cardiac cycle through a number of heartbeats, and in that way the heart is the same shape in each one and the alignment problem becomes simpler. However, not as much data is available.

By applying these techniques, the signal processor 124 maximizes imaging for contrast. Being able to perform these techniques on line and in real time is a major advantage over the conventional system.

Figure 3:
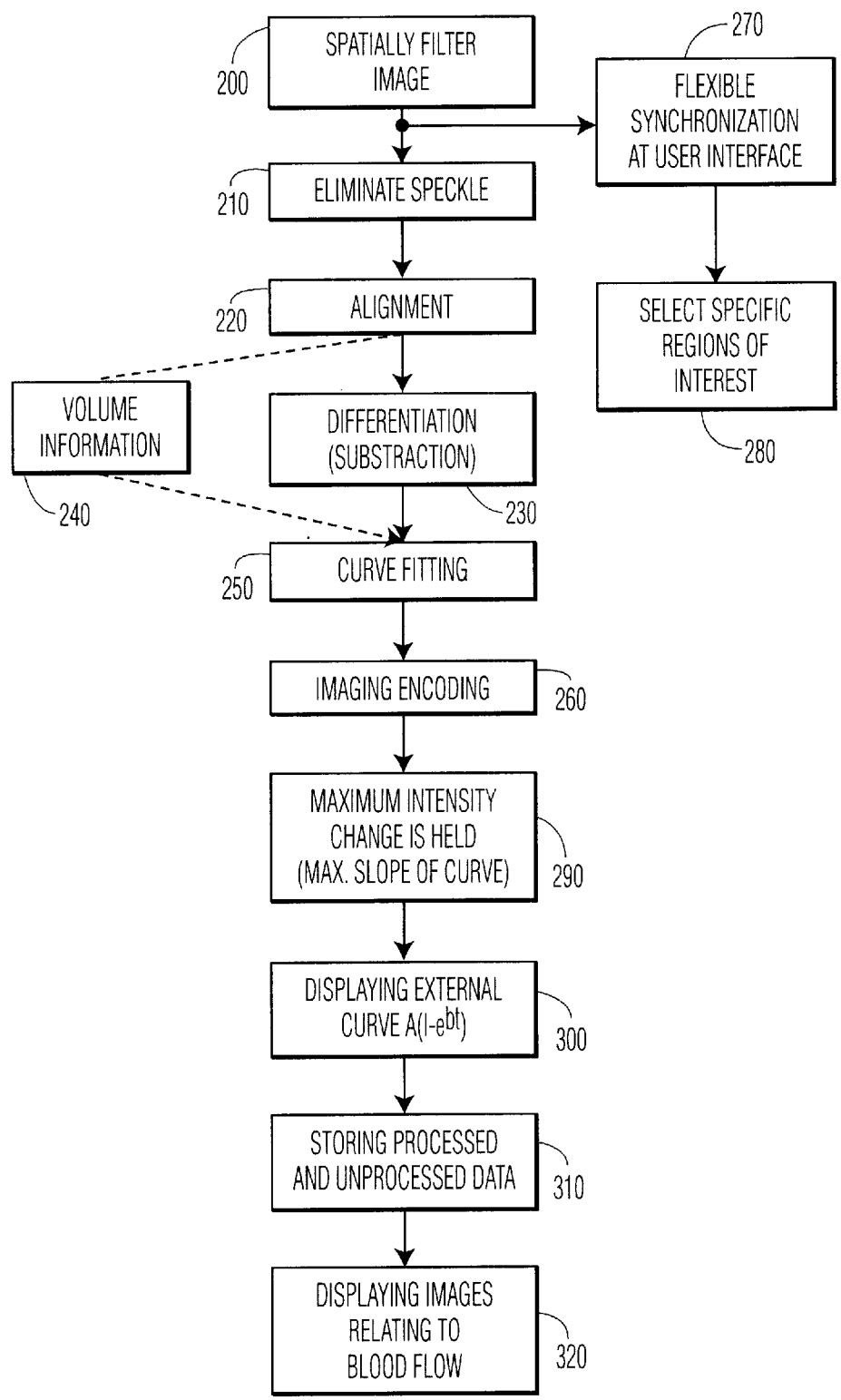
FIG. 3 is a flow chart showing operations for performing the processing of the image data received by the transducer array to determine blood flow according to an aspect of the present invention.

FIG. 3 is a flow chart showing operations for performing the processing of the image data received by the transducer array to determine blood flow according to an aspect of the present invention.

The operations are generally done sequentially, although many of the operations are optional, and the order of the operations is not important.

The first operation that the signal processor might perform according to the control routines 134 is to spatially filter the image in operation 200.

Ultrasound images are formed from narrow band or relatively narrow band energy and the spatial resolution is on the order the same as the wavelength of the energy that is being using to form the image. This means that the images are susceptible to an artifact as described previously, called speckle. Essentially, because the ultrasound coherently sums the energy received from all of the targets that are instantaneously within the ultrasound beam, it is conceivable, entirely possible and statistically probable that all of that energy will add up to be precisely zero even though there is definitely something present. If there is a piece of muscle, it is perfectly possible for the piece of tissue over at one point in the wavelength to destructively interfere with a piece of tissue over at the other point of the wavelength and the result is a zero signal. Consequently, little black spots called speckle are formed in the images Ultimately, a subtraction will be desired so that when two images are subtracted and each one of them has its own speckle pattern, the speckle patterns will not line up and there will be twice as much speckle. So an object is to attempt to eliminate the speckle. Ways to reduce or eliminate speckle include low-pass filtering, median filtering or compounding the images as shown in operation 210, although any other type of speckle reduction technique may be employed.

Another operation would be alignment as shown in operation 220 and the purpose of performing an alignment is to enable comparisons of images from one time to the next on the same piece of heart muscle in spite of the fact that the heart moved, the probe moved, the patient breathed, and any other motion introduced during the ultrasound testing. And again, a concept of alignment is that a general class of image processing algorithms would include but not be limited to translation, rotation, dilation and contraction, morphing.

Removal of the speckle may be performed, and then the alignment is performed, or the alignment may be performed first and then removal of the speckle may be performed.

An operation of subtraction or differentiation or some other operation designed to provide an output that represents a rate of change of the image is performed as shown in operation 230. Besides the rate of change, the doctor or technician may be interested in the volume of blood that is in a portion of the heart. It is very easy to see just by the image intensity that one starts with. What the doctor may ultimately be concerned with is the amount of oxygen reaching a particular part of the heart muscle as shown in operation 240 and that is the volume times the flow, which provides the amount of oxygen that reaches the heart muscle per second. If one were interested in volume information, the step of differentiating may be omitted. If both items of information were desired, both operations 230, 240 may be performed simultaneously and the product determined so as to provide the volume per unit of time.

During the differentiation, an image on the screen of the ultrasound imaging system 100 immediately after the destruction pulse would be mostly black and then the next image after that would have some brighter areas corresponding spatially to where some blood came back into the heart muscle and it would also probably have a large bright area in the chamber where the next heart beat of a massive volume of blood came in containing microbubbles.

The volume might have to determined another way because a curve is acquired, actually exponential curves of $A(1-e^{bt})$, which have plateaus and then this value represents the total volume. If drawn in real time as opposed to on line, but not real time, this value needs to be determined to show the flow over time in order to carry out the multiplication. The value b has to be known, but that value could be measured before destroying the microbubbles. Once a set number of microbubbles in the myocardium has been determined and then all of them are destroyed, a determination can be made as to how fast they come back, and the results can be processed and aligned. Based on how fast the microbubbles are returning, the slope from the previous determination, and the volume, the volume times the slope to get the flow, and the volumetric blood flow, can be determined.

Essentially, the ultimate determination is generally to produce an image that describes the rate of change of intensity which hopefully corresponds to blood volume by virtue of the fact that intensity is proportional to microbubbles and microbubbles is proportional to blood volume.

Using the above operations, the doctor or technician can just look at the brightness viewed upon the imaging, a sequence would begin and over the course of the sequence, there would be displayed bright areas where blood flow is occurring and dark areas where the blood flow is not occurring as quickly. In the conventional imaging system, a bright area would be an area having a lot of microbubbles. With the present invention, a bright area represents an area where microbubbles are being replenished quickly, such that the rate of bubble replenishment is high. Thus, the intensity represents the rate of bubble replenishment.

After the differentiation, some mathematical processing could be included, such as curve fitting as shown in operation 250. The device 100 may have a control to choose different types of curve-fitting, such as linear, exponential, piecewise linear, etc. Some type of imaging encoding as shown in operation 260 such as a mathematical encoding could be performed, so that the result of the mathematical processing which is providing a rate or the product of rate times flow is represented as a color or an intensity change or absolute intensity.

Of course, whatever data is generated may be exported into a transportable medium or into a permanent placement record.

What has been described to this point is an operation that operates on every frame as the same is output. However, a flexible synchronization technique 270 is possible. In some situations it would be advantageous to only operate on certain frames, ignoring intervening frames. Therefore, having a flexible way of synchronizing and selecting which frames are operated on, which can be based on physiological inputs from the patient such as an ECG or respiration, is desirable. The synchronizing and selecting may be set at a user interface.

Also, it would be advantageous to be able to select specific regions of interest within the overall image or have a zoom feature as shown in operation 280.

It is possible to include a zero order hold where the maximum intensity change is held as shown in operation 290. Here, at a point in time, an image would be frozen and the brightness would be the maximum rate of change seen over an entire acquisition period for that particular location. If the curve $A(1-e^{bt})$ is differentiated, there is a hump and then the value would decrease. The maximum value is probably going to occur at the beginning of the cycle after the microbubbles are destroyed because the exponential curve has a maximum slope at the beginning and then continually decreases.

It is also possible to produce a real time graph where the exponential curve $A(1-e^{bt})$ is drawn in real time in a second window on the display as shown in operation 300.

Another addition to the overall processing by the signal processor 124 according to the control routines 134 would be what is called siniloop memory as shown in operation 310. By pushing a button, a doctor or technician input the images into memory so that the images could be played back, at a later time. The processing is somewhat like that related to a solid state VCR. A button is pushed to start acquiring the images into the memory or a button can be pushed to review images that have already been acquired automatically by the memory. During this processing, new versions of the image are created. In this instance, there is an original raw image, and now there is also the processed raw image, both of which are stored in a recording medium. The doctor or the technician might not like the ultrasound imaging system's algorithm which processed that image, and wants to see the raw data again. The unprocessed data is essentially the images provided by the conventional ultrasound.

Of course, there is the operation 320 of displaying the images relating to blood flow and other post processing images. The results can also be presented as blood volume or blood velocity. The results can also be presented as a color coded or otherwise coded two-dimensional image which readily provides feedback during the contrast exam that the data is providing the required information necessary for a diagnosis of disease. The results can also be presented as time-dilution curves, or multiple curves being presented for multiple regions of interest as selected by the doctor or technician using a graphical user interface. Further, the device 100 may have controls to choose the type of display, such as showing a parametric image on one side and a regular image on the other side.

As noted previously, the order of the operations shown in FIG. 3 is not important, and most of the operations can be performed in any order. In addition, any of the selected data modes can be output from the ultrasound imaging system, either to a recording medium such as a magnetic medium, or to another computer system, via a network or the Internet.

It should also be noted that the present invention may also be applicable to magnetic resonance imaging (MRI) devices, and not just ultrasound imaging devices.

Still further, the present invention is not to be limited to blood flow, but may also be specifically designed to detect other types of fluids which flow throughout the body into cavities and/or tissues. Then the processing techniques mentioned above would be applied to the raw image data of the fluid which is of interest.

Still yet further, although the above techniques generally discussed two-dimensional ultrasound, the present invention may include displaying the processed images in three dimensions, to provide a three-dimensional display, and perhaps providing a bullseye display or a multiple slice display.

Although a few preferred embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A device for producing an image of a body part into which a contrasting agent has been introduced, comprising:
   an image detecting device modifying the contrasting agent to provide a modified image; and
   a processor acquiring and processing the modified image in real-time without storing the modified image so as to create an image which represents an actual condition of a rate of flow of blood in the body part at a particular instant in time.

2. The device as claimed in claim 1, further comprising a casing into which the image detecting device and the processor are integrally formed.

3. The device as claimed in claim 1, further comprising a single graphical user interface displaying the modified image and the image which represents the rate of flow of the blood.

4. The device as claimed in claim 1, further comprising a single graphical user interface displaying the modified image and the image which represents the blood volume or blood velocity.

5. The device as claimed in claim 1, wherein the processor processes the modified image on line.

6. The device as claimed in claim 1, wherein the device is an ultrasound imaging device.

7. The device as claimed in claim 1, wherein the device is a magnetic resonance imaging device.

8. The device as claimed in claim 1, wherein the processor spatially filters the modified image.

9. The device as claimed in claim 1, wherein the processor low pass filters the modified image to remove speckle.

10. The device as claimed in claim 1, wherein:
    the image detecting device detects a plurality of modified images over time; and the processor aligns the modified images by using ones of the modified images at a same time of a functioning cycle of the body part.

11. The device as claimed in claim 10, wherein the body part is a heart, and the same time of the functioning cycle is end-systole.

12. The device as claimed in claim 10, wherein the body part is a heart, and the same time of the functioning cycle is end-diastole.

13. The device as claimed in claim 1, wherein the processor aligns the modified images by using ones of the modified images at a plurality of case times of a functioning cycle of the body part.

14. The device as claimed in claim 10, wherein the processor performs the alignment by translation, rotation, dilation, contraction or morphing.

15. The device as claimed in claim 1, wherein:
the image detecting device detects a plurality of modified images over time; and
the processor compares the modified images to create the image which represents the rate of flow of the blood in the body part.

16. The device as claimed in claim 15, wherein the processor performs a differentiation or a subtraction on the modified images over time to make the comparison.

17. The device as claimed in claim 1, wherein:
the image detecting device detects a plurality of modified images over time; and
the processor uses the modified images to determine a volume of the blood in the body part.

18. The device as claimed in claim 1, wherein:
the image detecting device detects a plurality of modified images over time; and
the processor compares the modified images to create the image which represents the rate of flow of the blood in the body part, uses the modified images to determine a volume of the blood in the body part, and multiplies the volume by the rate of flow, to determine a volume per unit of time of the blood in the body part.

19. The device as claimed in claim 15, wherein the processor curve fits the modified images.

20. The device as claimed in claim 19, further comprising:
a control controlling the processor to select between different types of curve fitting.

21. The device as claimed in claim 15, wherein the processor image encodes the compared modified images so as to be represented as color or an intensity change or absolute intensity.

22. The device as claimed in claim 21, further comprising:
a control to turn the coloring on/off.

23. The device as claimed in claim 20, further comprising:
a display;
a control controlling the processor to process the compared modified images so that the compared modified images are colorized on one side of the display and not colorized on another side of the display.

24. The device as claimed in claim 1, further comprising:
a device which receives physiological inputs from a patient;
wherein
the image detecting device detects a plurality of modified images over time, and
the processor synchronizes or selects ones of the plurality of modified images based upon the physiological inputs.

25. The device as claimed in claim 1, further comprising:
an input device enabling a user to select a portion less than an entire region of the modified image, wherein the processor creates a portion of the image representing the rate of flow of the blood based upon the portion less than the entire region of the modified image.

26. The device as claimed in claim 1, wherein:
the image detecting device detects a plurality of modified images over time; and
the processor determines a maximum of the rate of flow of the blood over an entire acquisition period, and holds an image of the maximum rate of flow for display.

27. The device as claimed in claim 26, wherein the processor determines a slope of an exponential curve $A(1-e^{bt})$ of the plurality of modified images.

28. The device as claimed in claim 1, wherein:
the image detecting device detects a plurality of modified images over time; and
the processor determines a slope of an exponential curve $A(1-e^{bt})$ of the plurality of modified images, and creates an image with the image representing the rate of flow of blood in a first window, and the exponential curve in a second window.

29. The device as claimed in claim 1, further comprising:
a storage unit storing the modified image and the image representing the rate of flow of the blood.

30. The device as claimed in claim 1, further comprising:
a display which displays the image representing the rate of flow of the blood as a color coded image, a two-dimensional image, a time-dilution curve, or multiple curves representing multiple regions of the body part.

31. The device as claimed in claim 1, further comprising:
a display which displays the image representing the rate of flow of the blood as a three-dimensional image.

32. The device as claimed in claim 1, further comprising:
a control; and
a display displays the image representing the rate of flow of the blood as a parametric display on one side thereof and a regular image on the other side thereof based on operation of the control.

33. The device as claimed in claim 1, wherein:
the image detecting device detects a plurality of modified images over time; and
the processor low pass filters, median filters or compounds the modified image to remove speckle and aligns the modified images by using ones of the modified images at a same time of a functioning cycle of the body part.

34. The device as claimed in claim 1, wherein:
the image detecting device detects a plurality of modified images over time; and
the processor low pass filters, median filters or compounds the modified image to remove speckle, aligns the modified images by using ones of the modified images at a same time of a functioning cycle of the body part, and compares the aligned modified images to create the image which represents the rate of flow of the blood in the body part.

35. The device as claimed in claim 1, wherein the image detecting device destroys microbubbles which form the contrasting agent and detects new microbubbles which flow into the body part over time.

36. A device for producing an image of a body part into which a contrasting agent has been introduced, comprising:
an image detecting device detecting the contrasting agent in the body part to provide first images over time;

a processor integrally formed in the device and creating second images in real-time without storing the first images, said second images represent an actual condition of a rate of flow of blood in the body part based upon the first images at a particular instant in time; and a display which uses a same interface as that for the image detecting device and the processor, displaying the second images in real-time.

37. A device for producing an image of a body part into which a contrasting agent has been introduced, comprising:

an image detecting device detecting the contrasting agent in the body part to provide first images over time;

processor creating second images in real-time without storing the first images, said second images represent an actual condition of a rate of flow of blood in the body part based upon the first images at a particular instant in time; and a display displaying the second images in real-time.

* * * * *